United States Patent [19]

Twydell et al.

[11] Patent Number: 4,833,158

[45] Date of Patent: May 23, 1989

[54] METHOD OF COMBATING TERMITES

[75] Inventors: Roland S. Twydell; Jennifer M. Radcliffe, both of Sittingbourne, England

[73] Assignee: Shell Internationale Research Maatschappij B.V., The Hague, Netherlands

[21] Appl. No.: 133,983

[22] Filed: Dec. 17, 1987

[30] Foreign Application Priority Data

Jan. 15, 1987 [GB] United Kingdom ............... 8700838

[51] Int. Cl.$^4$ ..................... A01N 37/18; A01N 47/28
[52] U.S. Cl. ..................... 514/616; 514/594; 514/936; 514/946
[58] Field of Search ............... 514/594, 936, 946, 616

[56] References Cited

U.S. PATENT DOCUMENTS 4,005,223 1/1977 Sirrenberg et al. ............... 514/594
4,277,499 7/1981 Sirrenberg et al. ............... 514/594
4,698,365 10/1987 Anderson ........................... 514/594

FOREIGN PATENT DOCUMENTS 0161019 11/1985 European Pat. Off. .
1460419 1/1977 United Kingdom .

OTHER PUBLICATIONS

Su, Nan-Yao, et al, Journal of Economic Entomology, vol. 78, No. 6, pp. 1259-1263 (12/1985).

Primary Examiner—Douglas W. Robinson
Assistant Examiner—Zohreh A. Fay

[57] ABSTRACT

This invention provides a method of combating termites at a locus, which comprises treating the locus e.g. soil or timber with an acyl urea of the formula

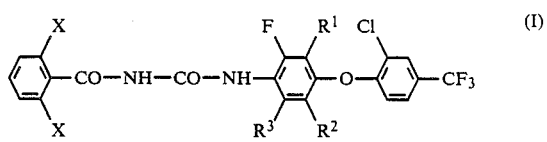

wherein one substituent X is a halogen atom or a merthyl group and the other is a halogen atom, a hydrogen atom or a methyl group, and each of $R^1$, $R^2$ and $R^3$ independently represents a hydrogen or fluorine atom; the use of acyl ureas of formula I for combating termites; and compositions for protecting timber against termite attack.

7 Claims, No Drawings

METHOD OF COMBATING TERMITES

This invention relates to a method of combating termites, to the use of certain acyl ureas for combating termites, to compositions for protecting timber against termite attack and to timber protected against termite attack.

Termites are insects of the order Isoptera, which can cause considerable structural damage to buildings in warmer climates, being present between latitude 42° N and 42° S. This damage may be prevented, or minimised, by the use of insecticidal compounds active against termites. Such compounds are conventionally applied either to the building or its component members, e.g. by treatment of timber components before incorporation into the building, or to soil area surrounding the building.

The majority of commercially available insecticides do not have the combination of biological and physicochemical properties necessary for effective termite control (e.g. activity against termites combined with long-term persistence), but the chlorinated hydrocarbon aldrin has proved effective. However, increased regulatory controls on chlorinated hydrocarbons have created a need for a termiticide which combines the necessary activity and persistence with a low mammalian toxicity.

UK Pat. No. 1,460,419 discloses acyl ureas of the formula

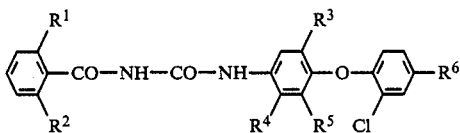

in which $R^1$ is fluorine, chlorine, bromine or methyl, $R^2$ is hydrogen, fluorine or chlorine, $R^3$ is hydrogen or chlorine, $R^4$ is hydrogen, chlorine or methyl, $R^5$ is hydrogen or chlorine, and $R^6$ is nitro or trifluoromethyl, and their use as insecticides.

Although the actual insecticide test examples in UK Pat. No. 1,460,419 are limited to the test species diamond-back moth (*Plutella maculipennis*), owlet moth (*Laphygma exigua*) and mustard beetle (*Phaedon cochleariae*), the introductory part of the description contains a long list of insect pests to which it is stated that the above compounds may be applied and this list includes "termites such as the eastern subterannean termite (*Reticulitermes flavipes*)".

European Patent Application Publication No. 161019 (EP-A-161019) (Applicant's ref. K 1955) discloses acyl ureas of formula

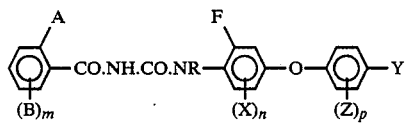

in which each of A and B independently represents a halogen atom or an alkyl group; m is 0 or 1; R represents a hydrogen atom or a group $-S.CO_2R^1$, $-S.SO_2R^1$ or $-S.NR^2R^3$, in which $R^1$ represents an optionally substitued alkyl or aryl group; $R^2$ represents an optionally substituted alkyl or aryl group; and $R^3$ represents an optionally substituted alkyl or aryl group, or a group of formula $-CO_2R^4$, $-SO_2R^4$, $-COR^4$, $-CO.CO_2R^4$, $-CO.NR^5R^6$ or $-SO_2NR^5R^6$, in which $R^4$ represents an optionally substituted alkyl or aryl group, and each of $R^5$ and $R^6$ independently represents an optionally substituted alkyl or aryl group; or $R^2$ and $R^3$ together or $R^5$ and $R^6$ together represent an optionally substituted alkylene group; in each case, the optional substituents for an alkyl or alkylene group being selected from halogen, alkoxy, alkoxycarbonyl, haloalkoxycarbonyl, alkylcarbonyl, haloalkylcarbonyl, alkylsulphonyl and haloalkylsulphonyl, and the optional substituents for an aryl group being selected from these substituents and also alkyl, haloalkyl, cyano and nitro; X represents a halogen atom or a cyano, nitro, alkyl or haloalkyl group; each of Y and Z independently represents a halogen atom or a cyano, nitro or haloalkyl group; n is 0, 1, 2 or 3; and p is 0, 1 or 2. These acyl ureas are described as having pesticidal, especially insecticidal and acaricidal activity, and test examples demonstrate activity against the insects *Spodoptera littoralis* and *Aedes aegypti* and the mite *Tetranychus urticae*. There is no mention in EP-A-161019 of termites per se.

It has now been found that certain acyl ureas, within the class defined in EP-A-161019, are surprisingly effective termiticides.

Accordingly the present invention provides a method of combating termites at a locus, which comprises treating the locus with an acyl urea of the formula

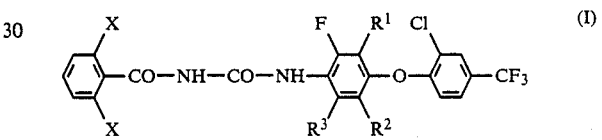

wherein one substituent X is a halogen atom or a methyl group and the other is a halogen atom, a hydrogen atom or a methyl group, and each of $R^1$, $R^2$ and $R^3$ independently represents a hydrogen or fluorine atom.

Preferably one substituent X is a halogen atom and the other is a hydrogen or halogen atom. Preferably the or each halogen atom is a fluorine or chlorine atom. Advantageously both substituents X are fluorine atoms.

Preferably each of $R^1$, $R^2$ and $R^3$ represents a hydrogen atom.

The acyl urea of formula I wherein both substituents X are fluorine atoms and each of $R^1$, $R^2$ and $R^3$ represents a hydrogen atom is the compound flufenoxuron.

The acyl ureas of formula I may be prepared by the processes described in EP-A-161019.

In order to facilitate the application of the acyl urea to the desired locus, the compound is normally formulated with a carrier and/or a surface-active agent.

A carrier in the present context is any material with which the active ingredient is formulated to facilitate application to the locus to be treated, or to facilitate storage, transport or handling. A carrier may be a solid or a liquid, including a material which is normally gaseous but which has been compressed to form a liquid, and any of the carriers normally used in formulating insecticidal compositions may be used. Preferably compositions according to the invention contain 0.5 to 95% by weight of active ingredient, though proportions as low as 0.001% may be useful in some circumstances.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminimium silicates; elements, for example carbon and sulphur; natural and synthetic resins, for example coumarone resins, polyvinyl chloride, and styrene polymers and copolymers; solid polycholorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone, isophorone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Polar organic liquids are particularly suitable, such as dimethyl formamide, dimethyl acetamide, dimethyl sulphoxide and N-methylpyrrolidone. Mixtures of different liquids are often suitable, for example a mixture of isophorone or "Shellsol K" (trade mark) with a polar organic solvent, such as N-methylpyrrolidone.

Pesticidal compositions are often formulated and transported in a concentrated form which is subsequently diluted by the user before application. The presence of small amounts of a carrier which is a surface-active agent facilitates this process of dilution. Thus preferably at least one carrier in such a composition is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

Pesticidal compositions may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3-10% w of a dispersing agent and, where necessary, 0-10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½-10% w of active ingredient.

Granules are usually prepared to have a size between 10 and 100 BS mesh (1.676-0.152 mm), and may be manufactured by agglomeration or impregnation techniques. Generally, granules will contain ½-75% w active ingredient and 0-10% w of additives such as stabilisers, surfactants, slow release modifiers and binding agents. The so-called "dry flowable powders" consist of relatively small granules having a relatively high concentration of active ingredient. Of particular interest in current practice are the water-dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulations contain 90% or more by weight of finely divided active material, 3-7% by weight of a blend of surfactants, which act as wetting, dispersing, suspending and binding agents, and 1-3% by weight of a finely divided carrier, which acts as a resuspending agent.

Emulsifiable concentrates usually contain, in addition to a solvent and, when necessary, co-solvent, 10-50% w/v active ingredient, 2-20% w/v emulsifiers and 0-20% w/v of other additives such as stabilisers, penetrants and corrosion inhibitors. Suspension concentrates are usually compounded so as to obtain a stable, non-sedimenting flowable product and usually contain 10-75% w active ingredient, 0.5-15% w of dispersing agents, 0.1-10% w of suspending agents such as protective colloids and thixotropic agents, 0-10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions are compositions which may be obtained by diluting a wettable powder or a concentrate with water. The said emulsions may be of the water-in-oil or of the oil-in-water type, and may have a thick 'mayonnaise'-like consistency.

Pesticidal compositions may also contain other ingredients, for example further active compounds possessing herbicidal, insecticidal or fungicidal properties, in accordance with the requirements of the locus to be treated and the treatment method.

The method of applying a compound of formula I to combat termites comprises applying the compound, conveniently in a composition comprising the compound of formula I and a carrier as described above, to a locus or area to be protected from the termites, such as soil or (directly to) timber subject to or subjected to infestation or attack by termites. The compound, of course, is applied in an amount sufficient to effect the desired action. This dosage is dependent upon many factors, including the carrier employed, the method and conditions of the application, whether the formulation is present at the locus in the form of a film, or as discrete particles, the thickness of film or size of particles, and the like. Proper consideration and resolution of these factors to provide the necessary dosage of the active compound at the locus to be protected are within the skill of those versed in the art. In general, however, the effective dosage of the compound of the invention at the locus to be protected—i.e. the dosage which the termite contacts—is of the order of 0.001 to 0.5% based on the total weight of the composition, though under some circumstances the effective concentration may be as little as 0.0001% or as much as 2%, on the same basis.

In one embodiment of this invention, acyl urea compounds of formula I are used to combat termites in the soil, thereby achieving indirect protection for any timber-based constructions erected on the treated soil. Suitable soil-based control is obtained by providing in the soil a termiticidally effective dosage of an acyl urea of formula I. For use in this manner, the acyl urea is suitably applied to the soil at a rate of from about 0.01 to about 10 kilograms per hectare. Good control of soil inhabiting termites is obtained at rates of from about 0.1 to about 5 kilograms per hectare and especially from about 0.5 to about 4 kilograms per hectare. The compound of formula I can conveniently be formulated for use as a granule or powder containing a solid diluent, impregnated with the compound, or as a suspension concentrate. Such formulations usually contain from about 1 to about 50% by weight of the compound. More effective control results when the formulation is physically lightly mixed with the topsoil. The compound of formula I can also be applied as a drench—that is, as a solution or dispersion of the compound in a suitable solvent or liquid diluent. Such drenches can be prepared by diluting with water a concentrate containing the compound of formula I, an emulsifying agent, and preferably an organic solvent, such as isophorone and/or N-methylpyrrolidone. The compound of formula I can be applied by band, furrow or side-dress techniques, and may be incorporated or not.

In another embodiment of the invention, acyl urea compounds of formula I are applied directly to timber, either before, during or after its incorporation into a building, thereby protecting it against damage from termite attack. For treatment of timber, the composition suitably contains a penetrant designed to facilitate penetration of the active ingredient to a significant depth in the timber, thereby ensuing that superficial surface abrasion will not generate a surface free from active ingredient and thus vulnerable to termite penetration. Examples of materials known for use as wood penetrants include paraffinic hydrocarbons, e.g. "Shellsol K" (trade mark) and low aromatic white spirit (LAWS), 2-ethoxyethanol, and methyl isobutyl ketone. Preferably the penetrant is 2-ethoxyethanol or methyl isobutyl ketone, optionally in association with isophorone and/or N-methyl pyrrolidone. It is useful in such timber treatment to incorporate "anti-bloom" agents, which counteract the tendency for the active ingredient to migrate to the surface ("blooming"), suitable materials being dibutyl phthalate and o-dichlorobenzene. Timber treatment compositions may also, if desired, contain fungicides (to prevent fungal attacks such as dry rot and wet rot), and/or pigments in order to combine termite protection with painting of the timber. In this context, painting will be understood to include not only the application of covering pigmentation (commonly white), but also the application of natural wood colouration in order to restore the appearance of weathered timber (e.g. as with treatments to red cedar external housing timbers). The actual application onto the timber may be carried out using conventional techniques including immersion of the timber in the liquid, and painting the liquid onto the timber by spray or brushing. The concentration of acyl urea active material in the treated timber should, of course, be sufficient to achieve the desired termiticidal effect. However, the total volume of formulated product taken up by the timber is limited by the absorption properties of the wood with respect to that formulation and will also vary according to the application procedure adopted (immersion or painting); hence the concentration of active ingredient in the formulation should be such as to produce the desired concentration in the treated timber. The formulation may be aqueous, as for example obtained by dilution of a conventional insecticide emulsifiable concentrate, or non-aqueous such as an undiluted emulsifiable concentrate. The organic solvent in such formulations will suitably be one of those previously described. The determination of the necessary parameters applicable to specific types of wood and particular treatment procedures can readily be determined by established techiques conventionally used by those skilled in the art. In general, however, the effective dosage of the compound in the wood may be as low as 10 ppm, with the maximum dosage dictated by cost considerations rather than biological efficacy. Often the lower dosage levels may initially give only a limited level of control, but achieve increased level of effect with more prolonged exposure.

The invention is illustrated in the following examples, all of which show the effect on the subterranean termite (*Reticulitermes santonensis*) of the compound flufenoxuron:

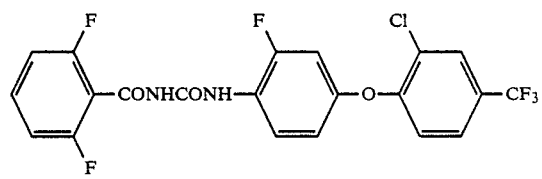

Example 1

Long term toxicity of impregnated wood and/or soil to mixed caste populations Treatments Four treatment regimes were employed.

1. One untreated pine sapwood block on top of treated soil.
2. One treated pine sapwood block on top of untreated soil.
3. One treated and one untreated pine sapwood block on top of untreated soil.
4. One untreated pine sapwood block on 1 cm deep layer of treated soil on top of untreated soil.
5. Untreated wood and soil control.

Treatments 1 to 4 were applied at 2 of test compound to give 100 and 10 ppm toxicant in dry soil or dry wood.

Application

Soil treatments-3 ml of acetone solution of test compound was applied by pipette onto 20 g of dried soil (75% general compost, 25% silver sand) in 75 ml glass bottles. These were rolled on a mixer for 1 hour and then placed uncapped in a vacuum oven at ambient temperature (21±3° C.) and 500 mm mercury vacuum (6.7×10$^4$Pa) overnight to remove the acetone. All soil samples were adjusted to 20% m/m water content with tapwater and rolled again for a further 1 hour prior to infestation.

Wood treatments-pine sapwood blocks were cut 15×15×7 mm and dried in a vacuum oven to constant weight. The volume of acetone required to almost saturate a typical wood block was determined at 0.7 ml and solutions of test compound in acetone were prepared such that this volume would provide the required dose of toxicant in the wood. Solutions were applied by means of a pipette and the exact volume delivered was adjusted for the weight of each individual block to ensure the accuracy of the dose applied.

Twelve samples were applied for each dose of every treatment including untreated controls.

Infestation

Each sample was infested with 36 or 37 termites comprising 10 nymphs, 25 workers, 1 secondary reproductive and at random the occasional soldier. This caste ratio was identical to that found in the insectary termite culture. Treatments were infested the day after application. Termites were placed on the soil surface and then the wood was introduced with the exception of treatment 4, where the termites were placed on 16 g of untreated soil and then covered with 4 g of treated soil and an untreated wood block. All bottles were loosely capped to prevent insect escape but allowing intake of air. These were held, arranged as randomised blocks, in a cabinet maintained at 26±1° C., 60±10% relative humidity throughout the test.

Assessments

Four assessments were carried out at monthly intervals. Three samples of each dose on every treatment including untreated controls were assessed at each period by carefully emptying them into a tray and counting the number and caste of the live termites present. These samples were discarded once they had been assessed. The data for total termite numbers was subjected to a two-way analysis of variance to give mean % effect relative to the untreated controls.

The results are set out in Table I.

TABLE I

| | | Long term exposure to treated soil or wood (3 replicates) | | | |
|---|---|---|---|---|---|
| | ppm test compound in dry | Mean % effect relative to untreated control (at days after treatment) | | | |
| Treatment | substrate | 28 | 56 | 84 | 112 |
| Treated soil + | 100 | 22 | 62 | 88 | 93 |
| untreated wood | 10 | 23 | 0 | 48 | 27 |
| Treated wood + | 100 | 83 | 100 | 100 | 100 |
| untreated soil | 10 | 3 | 47 | 96 | 93 |
| Treated and un- | 100 | 53 | 72 | 100 | 100 |
| treated wood + untreated soil | 10 | 0 | 72 | 32 | 100 |
| 1 cm layer treated | 100 | 0 | 15 | 100 | 100 |
| soil on untreated soil + untreated wood | 10 | 0 | 0 | 60 | 56 |
| Untreated wood/soil Control | 0 | 0 | 0 | 0 | 0 |
| (Total No. surviving on Control) | — | (20) | (11) | (8) | (5) |
| Least significant difference (LSD), treatments to Controls P = 0.05 | — | 41 | 76 | 65 | 89 |

Example 2

Topical application tests

Solutions of test compound in acetone were topically applied to the ventral abdomen of worker or nymph castes, anaesthetised with carbon dioxide, by means of a Hamilton syringe and micro-applicator.

All termites were held in 5 cm diameter plastic petri dishes containing 5 g of untreated soil (75% general compost, 25% silver sand) with a pine sapwood block for food. This system was adjusted to 10% water content and maintained in a glass tank at 21±2° C. and 90% relative humidity throughout the test period.

Assessments

Mortality was assessed over the following month and all dead termites were removed from each dish at inspection. The data selected were adjusted for control mortality using Abbotts formula:

Adjusted % mortality treatment $T =$ $$\frac{\% \text{ mortality } T - \% \text{ mortality Control}}{100 - \% \text{ mortality Control}} \times 100$$

The results are set out in Table II below.

TABLE II

| Treatments | Replicate | % Mortality (at days after treatment) | | | | | | | | |
|---|---|---|---|---|---|---|---|---|---|---|
| | | 1 | 2 | 3 | 6 | 8 | 10 | 13 | 16 | 27 |
| Control 10 | 1 | 10 | 20 | 20 | 30 | 30 | 30 | 50 | 50 | 100 |
| Workers 0.5 ul | 2 | 10 | 10 | 10 | 10 | 10 | 10 | 20 | 30 | 70 |
| acetone | 3 | 0 | 0 | 0 | 0 | 0 | 0 | 0 | 0 | 70 |
| | mean | 7 | 10 | 10 | 13 | 13 | 13 | 23 | 27 | 80 |
| | Adjusted mean | 0 | 0 | 0 | 0 | 0 | 0 | 0 | 0 | 0 |
| 10 Workers | 1 | 0 | 0 | 0 | 10 | 30 | 50 | 50 | 60 | 100 |
| 5 ug test | 2 | 10 | 20 | 20 | 30 | 30 | 60 | 60 | 80 | 100 |
| compound | 3 | 10 | 20 | 20 | 20 | 50 | 70 | 70 | 70 | 100 |
| | mean | 7 | 13 | 13 | 20 | 37 | 60 | 60 | 70 | 100 |
| | Adjusted mean | 0 | 5 | 5 | 7 | 27 | 54 | 49 | 59 | 100 |
| 10 Workers | 1 | 0 | 10 | 10 | 10 | 10 | 20 | 20 | 30 | 90 |
| 0.5 ug test | 2 | 0 | 0 | 0 | 10 | 30 | 30 | 30 | 40 | 70 |
| compound | 3 | 10 | 10 | 10 | 20 | 30 | 60 | 70 | 70 | 80 |
| | mean | 3 | 7 | 7 | 13 | 23 | 37 | 40 | 47 | 80 |
| | Adjusted mean | 0 | 0 | 0 | 0 | 12 | 24 | 22 | 27 | 0 |
| Control 10 | 1 | 0 | 0 | 10 | 10 | 10 | 10 | 20 | 50 | 100 |
| nymphs 0.5 ul | Adjusted | 0 | 0 | 0 | 0 | 0 | 0 | 0 | 0 | — |

TABLE II-continued

| Treatments | Replicate | % Mortality (at days after treatment) | | | | | | | | |
|---|---|---|---|---|---|---|---|---|---|---|
| | | 1 | 2 | 3 | 6 | 8 | 10 | 13 | 16 | 27 |
| acetone + 5 untreated workers 10 nymphs 5 ug test compound | 1 | 0 | 0 | 0 | 20 | 20 | 20 | 20 | 40 | 100 |
| | Adjusted | 0 | 0 | 0 | 0 | 0 | 0 | 0 | 0 | — |
| | 1 | 0 | 0 | 0 | 0 | 50 | 60 | 100 | 100 | 100 |
| | 2 | 0 | 0 | 0 | 20 | 50 | 100 | 100 | 100 | 100 |
| | 3 | 0 | 10 | 10 | 20 | 50 | 60 | 70 | 90 | 100 |
| | mean | 0 | 3 | 3 | 13 | 50 | 73 | 90 | 97 | 100 |
| | Adjusted mean | 0 | 3 | 0 | 5 | 44 | 70 | 88 | 91 | — |
| + 5 untreated workers | 1 | 0 | 20 | 20 | 20 | 20 | 60 | 60 | 80 | 100 |
| | 2 | 0 | 0 | 0 | 0 | 60 | 100 | 100 | 100 | 100 |
| | 3 | 0 | 0 | 0 | 0 | 20 | 20 | 20 | 20 | 100 |
| | mean | 0 | 7 | 7 | 7 | 33 | 60 | 60 | 67 | 100 |
| | Adjusted mean | 0 | 7 | 7 | 0 | 18 | 50 | 50 | 43 | — |

Example 3

Comparative topical application tests

Comparative topical application test were made using compounds of the formula

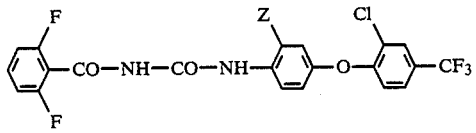

(i) in accordance with the invention wherein Z is F (the compound being flufenoxuron), (ii) for comparison purposes wherein Z is H (the compound of Example 2 of UK Pat. No. 1,460,419) and (iii) for comparison purposes wherein Z is Cl (in accordance with UK Pat. No. 1,460,419).

Each of the three test compounds was dissolved in acetone to give solutions having concentrations of compound of 30, 10, 3, 1 and 0.3 mg/ml.

Groups of 10 workers of subterranean termite (Reticulitermes santonensis) were treated by topical application on the ventral abdomen of 0.5 microlitres of solution by means of a Hamilton syringe an microapplicator. Three replicates were employed for each treatment including a blank acetone control. Post treatment, each group was held in 5 cm diameter vented plastic petri dishes containing 5 g of untreated soil (75% general compost, 25% silver sand adjusted to 10% water content) with a pine sapwood block (5×10×10 mm) as food. These petri dishes were maintained in a glass tank at 21±2° C. and 90% relative humidity throughout the test period. The soil in each dish was moistened with 0.2 ml of water once a week as this was found to improve the viability of the termites.

Assessments were carried out periodically over the following 31 days and any dead workers were removed at each evaluation. The test was discontinued at this time as sporadic fungal growth gave random mortality throughout after this period.

In each case an $LD_{50}$ (the dosage of compound required to kill half of the test species) was calculated from the mortality figures at 2 weeks and 3 weeks. Results are given in Table III following.

TABLE III

| Compound | Time after treatment | $LD_{50}$ (micrograms) |
|---|---|---|
| (i) flufenoxuron (Z = F) | 2 weeks | 20 |
| | 3 weeks | 1 |
| (ii) comparative (Z = H) | 2 weeks | more than 30 |

TABLE III-continued

| Compound | Time after treatment | $LD_{50}$ (micrograms) |
|---|---|---|
| | 3 weeks | more than 30 |
| (iii) comparative (Z= Cl) | 2 weeks | more than 30 |
| | 3 weeks | more than 30 |

We claim:

1. A method of combating termites at a locus infested with termites, said method comprising treating said locus with a termiticidally effective amount of an acyl urea of the formula

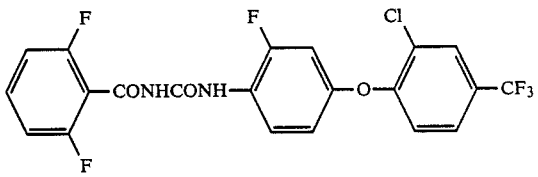

2. The method of claim 1 wherein the locus comprises soil or timber infested with termites.

3. The method of claim 2 wherein said soil or timber is treated with said acyl urea by application of a composition comprising said acyl urea and a carrier.

4. A method of protecting a locus subject to termite attack against such attack, said method comprising treating said locus with an amount of acyl urea compound of the formula

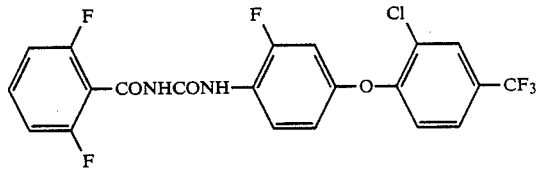

5. The method of claim 4 wherein said locus comprises soil or timber.

6. The method of claim 5 wherein said soil or timber is treated with said acyl urea by application of a composition comprising said acyl urea and a carrier.

7. Timber impregnated at least at a surface with a termiticidally effective amount of a termiticidally effective acyl urea compound having the formula

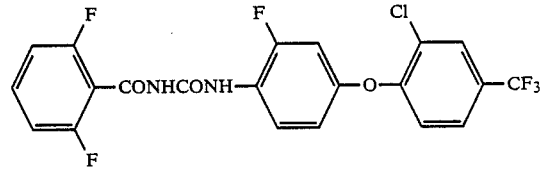

* * * * *

UNITED STATES PATENT AND TRADEMARK OFFICE
CERTIFICATE OF CORRECTION

PATENT NO. : 4,833,158
DATED : May 23, 1989
INVENTOR(S) : ROLAND S. TWYDELL ETAL

It is certified that error appears in the above-identified patent and that said Letters Patent is hereby corrected as shown below:

Claim 4, line 3 (column 10, line 42) change " an amount" to -- a termiticidally effective amount --

Claim 7 lines 2 and 3 ( column 10, lines 58 and 59), after "of" delete " a termiticidally effective."

Signed and Sealed this

Tenth Day of October, 1989

Attest:

DONALD J. QUIGG

*Attesting Officer*    *Commissioner of Patents and Trademarks*